United States Patent
Engel et al.

(10) Patent No.: US 9,541,507 B2
(45) Date of Patent: Jan. 10, 2017

(54) COLOR-BASED FOREIGN OBJECT DETECTION SYSTEM

(71) Applicants: Stephen J. Engel, East Northport, NY (US); Robert J. Christ, Brentwood, NY (US); John Madsen, Commack, NY (US); Jerrell A. Nardiello, Hicksville, NY (US); Skylar Blaiz Cobb, Hermosa Beach, CA (US); Scott W. Shaffar, Irvine, CA (US)

(72) Inventors: Stephen J. Engel, East Northport, NY (US); Robert J. Christ, Brentwood, NY (US); John Madsen, Commack, NY (US); Jerrell A. Nardiello, Hicksville, NY (US); Skylar Blaiz Cobb, Hermosa Beach, CA (US); Scott W. Shaffar, Irvine, CA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 234 days.

(21) Appl. No.: 14/469,125

(22) Filed: Aug. 26, 2014

(65) Prior Publication Data

US 2016/0061746 A1 Mar. 3, 2016

(51) Int. Cl.
| | |
|---|---|
| G01J 3/46 | (2006.01) |
| G01N 21/94 | (2006.01) |
| G06K 9/00 | (2006.01) |
| G06K 9/46 | (2006.01) |
| G01N 21/88 | (2006.01) |

(52) U.S. Cl.
CPC .......... *G01N 21/94* (2013.01); *G01N 21/8851* (2013.01); *G06K 9/00664* (2013.01); *G06K 9/4652* (2013.01)

(58) Field of Classification Search
CPC .......... G01N 21/94; G01N 21/474; G01J 3/02; G01J 3/50; G01J 3/46; G01J 3/524
USPC ................................... 356/402–425
See application file for complete search history.

(56) References Cited

U.S. PATENT DOCUMENTS

| | | | |
|---|---|---|---|
| 5,085,325 A | 2/1992 | Jones et al. | |
| 5,533,628 A | 7/1996 | Tao | |
| 6,064,429 A * | 5/2000 | Belk | G01N 21/94 348/128 |
| 6,493,620 B2 | 12/2002 | Zhang | |

(Continued)

OTHER PUBLICATIONS

V Leemans et al: "Defect segmentation and 'Jonagold' apples using colour vision and a Bayesian classification method", Computers and Electronics in Agriculture, vol. 23, No. 1, Jun. 1, 1999, pp. 43-53.

(Continued)

*Primary Examiner* — Abdullahi Nur
(74) *Attorney, Agent, or Firm* — Tarolli, Sundheim, Covell & Tummino LLP

(57) ABSTRACT

Systems and methods are provided for detecting foreign objects in or on a subject of interest. A first set of images is captured of a sample subject known to be free of foreign objects. A plurality of colors from a defined color palette are classified according to a color content of the first set of images into at least first and second classes. A second set of images of the subject of interest are captured. It is determined that a foreign object is present in or on the subject of interest if a color from the first class is present in the second set of images.

20 Claims, 3 Drawing Sheets

(56) References Cited

U.S. PATENT DOCUMENTS

| | | | |
|---|---|---|---|
| 7,848,566 B2 | 12/2010 | Schneiderman | |
| 8,553,086 B2 | 10/2013 | Springett et al. | |
| 2011/0131279 A1* | 6/2011 | Karnik | G06Q 10/107 709/206 |

OTHER PUBLICATIONS

Celenk M: "A Bayesian approach to object detection in color images", System Theory, 1998. Proceedings of the Thietieth Southeastern Symposi Um on Morgantown, WV, USA Mar. 8-10, 1998, New York, New York, pp. 196-199.

Bosch et al: "Which is the best way to organize/classify images by content?" Image and Vision Computing, Elsevier, Guilford, GB vol. 25, No. 6, Apr. 6, 2007, pp. 778-791.

International Search Report for Application No. PCT/US2015/043141 dated Oct. 26, 2015.

Argyros, et al.: "*Real-Time Tracking of Multiple Skin-Colored Objects with a Possibly Moving Camera*", T. Pajdla and J. Matas (Eds.): ECCV 2004, LNCS 3023, pp. 368-379, 2004.

Baidyk, et al.: "Texture Recognition with Random Subspace Neural Classifier", *WSEAS Transactions on circuits and systems* 4.4 (2005): 319-324.

Hu, et al.: "Foreground Objects Recognition in Video Based on Bag-of-Words Model", Nov. 2009, Foreground objects recognition in video based on bag-of-words model. In *Pattern Recognition*, 2009. CCPR 2009. Chinese Conference on (pp. 1-5), IEEE.

Rasool, et al.: "*An Autoadaptive Edge-Detection Algorithm for Flame and Fire Image Processing*", International Journal of Computer & Organization Trends, vol. 3, Issue 11, Dec. 2013, ISSN: 2249-2593, pp. 537-542.

Taqa, et al.: "*Constructing Pornographic Images Detector Based on Naïve Bayesian Classifier*", , J. Education Sci. College Education University Mosul, 23(1): 84, ISSN 1812-125X.

\* cited by examiner

COLOR-BASED FOREIGN OBJECT DETECTION SYSTEM

TECHNICAL FIELD

This application relates generally to quality control operations, and more specifically, to a color-based foreign object detection system.

BACKGROUND

Foreign object debris is a substance, debris, or article alien to a product or system that would potentially cause damage, or malfunction. Foreign object damage is any damage attributed to a foreign object, that is, any object that is not part of the product, that can be expressed in physical or economic terms and may or may not degrade the product's required safety or performance characteristics. FOD is an acronym often used, particularly in aviation, to describe both the damage done to products by foreign objects, and the foreign objects themselves. In the aviation industry alone, it is believed that foreign object damage causes as much as thirteen billion dollars per year in direct and indirect costs, including delays, aircraft changes, incurred fuel costs, and unscheduled maintenance.

SUMMARY

In accordance with one example, a method is provided for detecting foreign objects in or on a subject of interest. A first set of images is captured, for example, as a series of individual images or as a video stream, of a sample subject known to be free of foreign objects. A plurality of colors from a defined color palette are classified according to a color content of the first set of images into at least first and second classes. A second set of images of the subject of interest are captured. It is determined that a foreign object is present in or on the subject of interest if a color from the first class is present in the second set of images.

In accordance with another example, a system is provided for detecting foreign objects in or on a subject of interest. The system includes an imaging system and a system control configured to instruct the imaging system to capture a first set of images of a sample subject known to be free of foreign objects. A color selection component is configured to select a plurality of colors from a defined color palette according to a color content of the first set of images. The system control is further configured to instruct the imaging system to capture a second set of images of the subject of interest and notify a user if a selected color is present in the second set of images.

In accordance with yet another example, a non-transitory computer readable medium is provided. A system control is configured to instruct an imaging system to capture a first set of images of a sample subject known to be free of foreign objects. The system control includes an imager interface configured to receive the captured first set of images and a user interface configured to receive an input from a user. A color selection component is configured to classify a plurality of colors from a defined color palette according to a color content of the first set of images into at least first and second classes. The system control is also configured to instruct the imaging system to capture a second set of images of a subject of interest, notify a user when color from the first class is present in the second set of images, and receive an input from the user via the user interface indicating if the color represents a foreign object in the subject of interest.

BRIEF DESCRIPTION OF THE DRAWINGS

The features, objects, and advantages of the hybrid qubit assembly will become more apparent from the detailed description set forth below when taken in conjunction with the drawings, wherein.

DETAILED DESCRIPTION

Described herein is a foreign object detection system that searches for deviations from an expected color content of a product or environment to detect the presence of foreign objects. It will be appreciated that the word "color" is used broadly herein to describe an intensity profile of an object across multiple wavelengths, as represented by a set of intensity values received at an appropriate detector. Accordingly, a given location on an object can have multiple "colors" based on the illumination, detector angle, and distance from the object (e.g., due to pixel blending at increased distances) and each of these colors is intended to be captured by the system and recorded as part of the expected color content of the object. It will be appreciated that a given "color" can include intensities for wavelengths in the visible, infrared, and ultraviolet spectra, and that the intensity for a given wavelength can be measured during active illumination using light of the appropriate wavelength or under ambient lighting. In one implementation, the color of a given pixel is indicated as intensity values at a detector for red, green, and blue light.

The foreign object detection system annunciates the presence of foreign object debris (FOD) in manufactured assemblies before they "escape" from the manufacturing facility to a next assembly, or more seriously, to the customer/end user. In one implementation, the system includes an imaging system, such as a digital video camera, a display, and an LCD display, and a portable computer with machine vision software algorithms that process incoming video data and identify foreign objects in the field of view by their color. When a foreign object is detected, the system alerts the operator so that the debris can be removed before the next assembly step where they might be encapsulated within the assembly. In one implementation, the foreign object detection system can be implemented in a structure resembling a flashlight, as inspectors currently use standard flashlights to visually scan for FOD, and an inspector who is comfortable using a flashlight should find the proposed system to be very familiar. In another implementation, the system could be implemented in a wearable computer with an optical head-mounted display.

Figure 1:
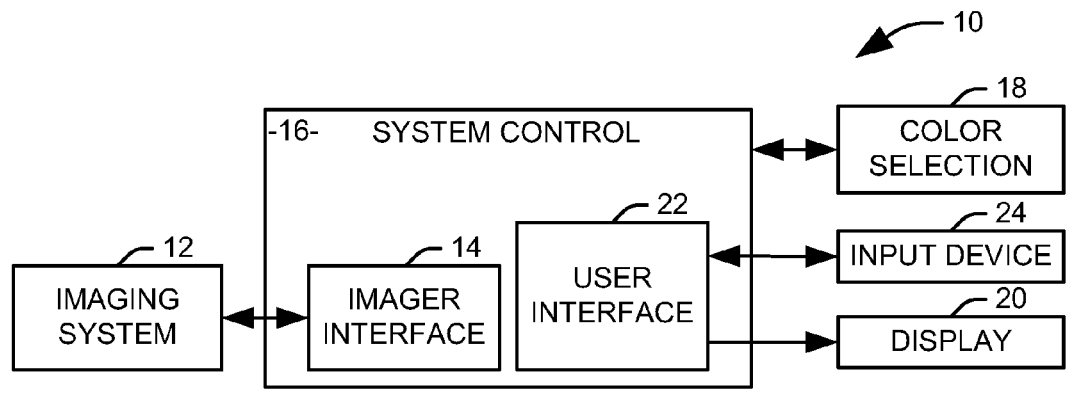
FIG. 1 illustrates an example of a foreign object detection system.

FIG. 1 illustrates an example of a foreign object detection system 10. The system includes an imaging system 12 instructed to capture a first set of images of a sample subject known to be free of foreign objects by an imager interface 14 at a system control 16. It will be appreciated that the set of images can include a series of individual images or frames within a video stream. For the purpose of this application, a "subject" can be any product or environment in which the present of foreign objects is undesirable. For example, the subject of interest can be an interior of an aircraft. The sample subject is selected to represent the subject of interest in every way besides the known absence of foreign objects. For example, the sample subject could be an already inspected product of the same type as the subject of interest or even the subject of interest itself at a time at which it is known to be free of foreign objects. It will be appreciated that the imaging system 12 can be configured to detect light at a plurality of wavelengths to give a set of a plurality of intensity values for each pixel, defining a color for that pixel.

A color selection component 18 is configured to select a plurality of colors from a defined color palette according to a color content of the first set of images. For example, the defined color palette can contain all possible colors that can be formed from measured wavelengths, binned at a desired level of resolution. In one example using eight-bit red, green, and blue values, the bins for each can have a width of five, with thirty-one bins for each wavelength and 29,791 possible colors. In one implementation, the distribution of colors from the first set of images can be determined via a naïve Bayesian classification for each color, with a probability that a given color is part of the background, P(S|C), calculated and a color selected if the probability is below a predetermined threshold. In this example, the probability that each color will appear, given that it is part of the sample subject, P(C|S), can be estimated from first set of sample images, and the other probabilities needed to calculate, P(C) and P(S) can be estimated from historical testing data. In another example, all colors that are not present in the first set of images are selected. Finally, all colors falling outside of a predetermined distance from the colors in the first set of images can be selected. It will be appreciated that regardless of whether high probability or low probability colors are explicitly identified by the system, any division of the colors into "allowed" and "disallowed" classes inherently represents a selection of the colors that should not be present in the subject of interest, and these colors are treated as the selected colors for the purpose of clarity hereforward.

The imaging system 12 can then be instructed by the system control to capture a second set of images of the subject of interest. Since all of the possible colors have been preclassified, the images can be processed in real-time to determine if any pixels in the images have a color from the selected plurality of colors are present. If so, the pixels can be indicated to a user at an associated display 20. For example, the pixels having colors from the plurality of selected colors can be highlighted or shown in color while other pixels are shown in grayscale. Alternatively, text labels can be used to notify the user if no pixels having one of the selected colors is present (e.g., "All clear"), Accordingly, the displayed data presented to the user is augmented to ensure that anomalies in the images are emphasized, greatly increasing the likelihood that foreign objects in or on the subject of interest will be detected.

In one implementation, the user can confirm or reject the presence of a foreign object in the indicated location at a user interface 22 via an appropriate input device 24. If the user confirms the foreign object, no change in the selected plurality of colors is made. If the user indicates that no foreign object is present, one or more colors associated with the detected foreign object can be removed from the plurality of selected colors, such that objects have the same color, or optionally, a range of similar colors around the detected color, will not be highlighted for the user. Accordingly, training of the system can be continued even during the real-time scanning of the subject of interest, enhancing the accuracy of the foreign object detection.

Figure 2:
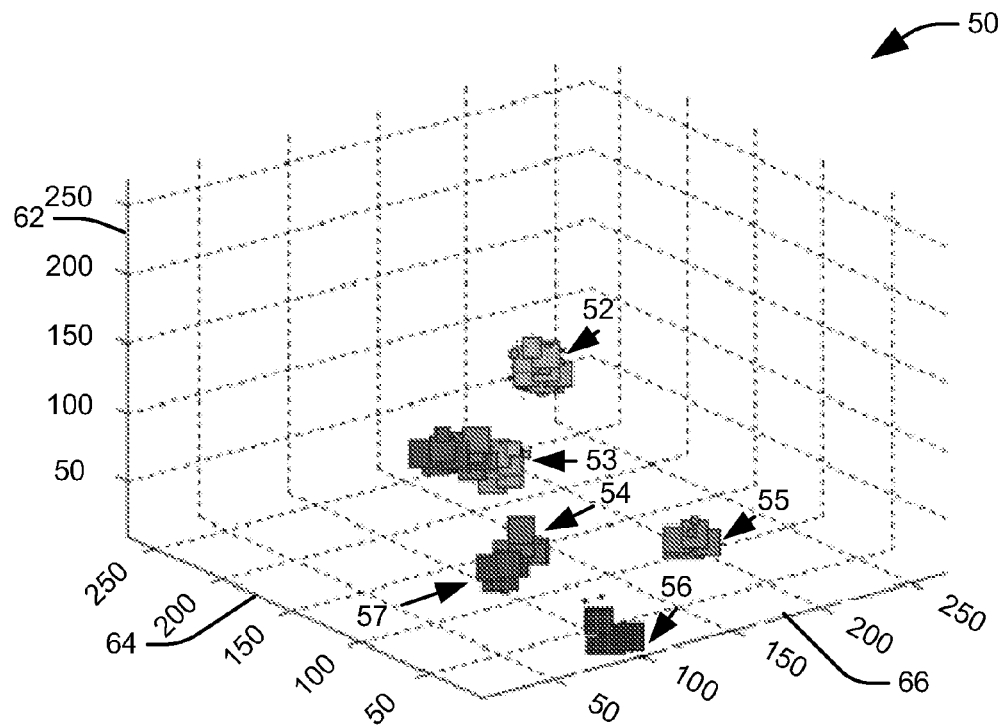
FIG. 2 is a representation of a plurality of foreign objects in a red-green-blue color space.

FIG. 2 is a representation 50 of a plurality of foreign objects 52-57 in a red-green-blue (RGB) color space. Examples of foreign objects can include cotter pins, tape, washers, and other small objects that might be utilized in a workspace associated with a product and left behind. The color space is defined by three axes, 62, 64, and 66, each representing a range of eight-bit values for one of the red, blue, and green color content of a given pixel. It will be appreciated that the foreign objects 52-57 are each represented as a substantial range of colors, as the distance from the imager to the object, variations among the objects, and variations in illumination can all alter the color content received at the imager. This makes it difficult to precisely define the colors associated with a given foreign object for classification. The image of the current application, however, focuses on learning the background colors for a given subject. As a result, the entire range of colors associated with each object can be accounted for, as well as colors associated with foreign objects that were unexpected and thus not accounted for in a detection system.

Figure 3:
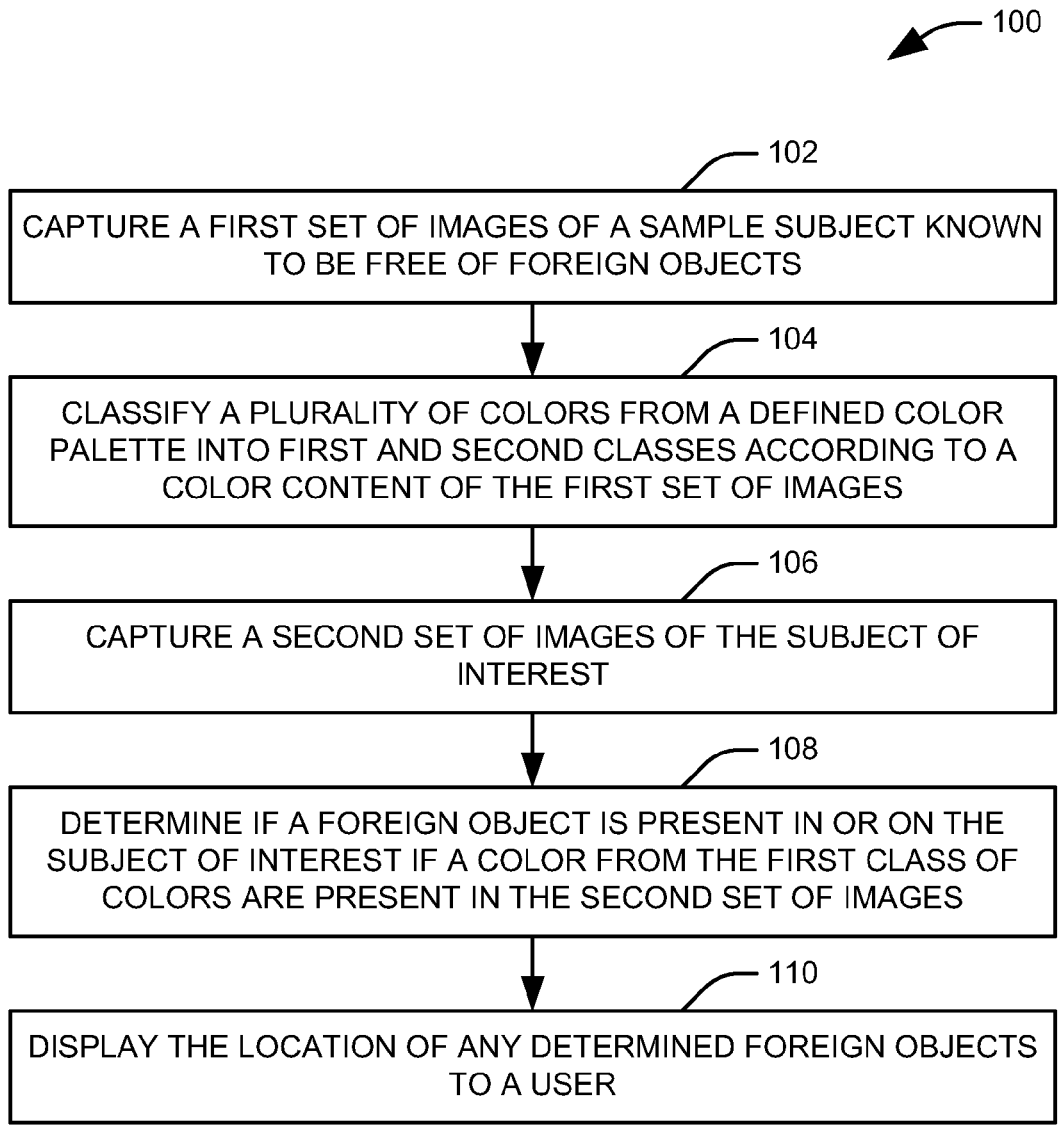
FIG. 3 illustrates an example of a method for detecting foreign objects in or on a subject of interest.
Figure 4:
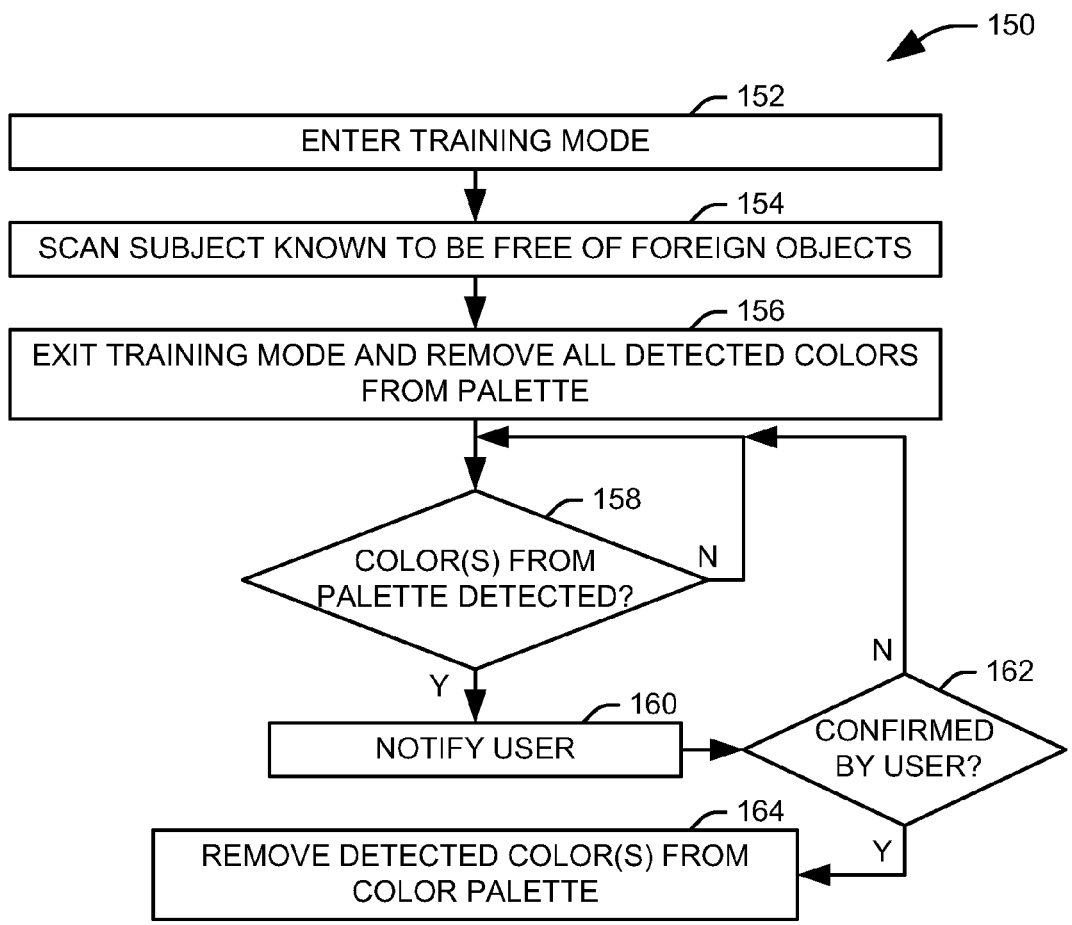
FIG. 4 illustrates another example of a method for detecting foreign objects in or on a subject of interest.

In view of the foregoing structural and functional features described above, methods in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect the present invention.

FIG. 3 illustrates an example of a method 100 for detecting foreign objects in or on a subject of interest. At 102, a first set of images is captured of a sample subject known to be free of foreign objects. The first set of images can be captured, for example, as a series of individual images or as a video stream. It will be appreciated that a sample subject can be any product or environment expected to share a color palette of the subject of interest and can include, for example, another product of the same type or a portion of the subject of interest that has been inspected by a human operator. The first set of images represents the colors associated with the subject of interest in the absence of foreign objects, referred to herein as "background" colors. In one implementation, a plurality of intensity values, each associated with a specific wavelength of visible, infrared, or ultraviolet light, are captured for each pixel of the first set of images, and each of the plurality of intensity values to a desired resolution, such that the defined color palette is defined according to the desired resolution and a number of intensity values in the plurality of intensity values for each pixel. For example, the intensity values can be represented as eight-bit red, green, and blue values, and the quantization can include rounding the intensity values to multiples of five, with thirty-one possible quantized values for each wavelength and 29,791 possible colors.

At 104, a plurality of colors from a defined color palette are classified into a first class and a second class according to a color content of the first set of images. Effectively, the selection classifies the entire color palette into background colors and non-background colors, and stores one of the two classes of colors in order to discriminate between colors expected in the subject of interest and colors likely to be associated with foreign objects. To this end, the colors can be classified via a modified naïve Bayesian classification, using the first set of images as training data, to provide the first and second classes of colors. Alternatively, all colors of the plurality of colors appearing in the first set of images can be assigned to the second class and all other colors of the plurality of colors can be assigned to the first class.

At 106, a second set of images is captured of the subject of interest. In one example, a user with a handheld or worn imaging sensor can direct the imager over the subject of interest to ensure that a variety of lighting conditions and distances from the object are recorded. Alternatively, the imager can be moved by an automated device or be stationary, with the subject of interest moved into its field of view. At 108, it is determined if a foreign object is present in or on the subject of interest if a color from the first class of colors is present in the second set of images. It will be appreciated that, since the colors are classified in advance of the scan of the subject of interest, the recognition of colors representing foreign objects can be performed in real-time, allowing a user to immediately respond to the presence of the foreign object.

At 110, a location of any determined foreign objects are displayed to a user, assuming any foreign object is determined to be present. For example, the location can be indicated by displaying a captured image of the second set of images to the user with the location of the foreign object displayed in color and a remainder of the image displayed in grayscale, displaying the image to the user with the location of the foreign object highlighted in a preselected color or shape, or by displaying a text message to a user. It will be appreciated that this display can be immediate with the real-time scanning process, so there is no need to allow the scan of the subject of interest to be completed before notifying the user. Accordingly, in one implementation, the system can receive feedback from the user that the foreign object determined to be present is not a foreign object, determine a set of colors associated with the foreign object, and transfer the determined set of colors from the first class to the second class. Accordingly, when the system does produce a false alarm, the user input can be used to retrain the system to avoid future false alarms based on the same color.

FIG. 4 illustrates another example of a method 150 for detecting foreign objects in or on a subject of interest. At 152, a foreign object detection system enters a training mode. In the training mode, all images captured by the foreign object detection system are presumed to be free of foreign objects, such that the captured data can be used to train the system. At 154, the system is transitioned across a subject, such as a portion of the subject of interest or another subject that is known to be free of foreign objects to capture images having different distance from the subject and different lighting conditions.

At 156, the foreign object detection system exits the training mode, and all colors found in the captured training data are removed from a color palette containing all possible colors for the detector, leaving only colors expected to be associated with foreign objects. The system scans for colors from the palette, which can represent foreign objects, at decision block 158. When a color is located from the colors remaining in the color palette (Y), the method advances to 160, where the user is notified that a potential foreign object has been located and prompted to confirm the finding. The method then awaits an input from the user at decision block 162. If the user indicates that the potential foreign object is a foreign object (Y), the method returns to 158 to continue the scan for foreign objects. If the user indicates that the detected object represents a false alarm, the method continues to 164, where all of the colors associated with the detected foreign object are removed from the palette of colors expected to be associated with foreign objects. The method then returns to 158 to continue the scan of the subject of interest.

Figure 5:
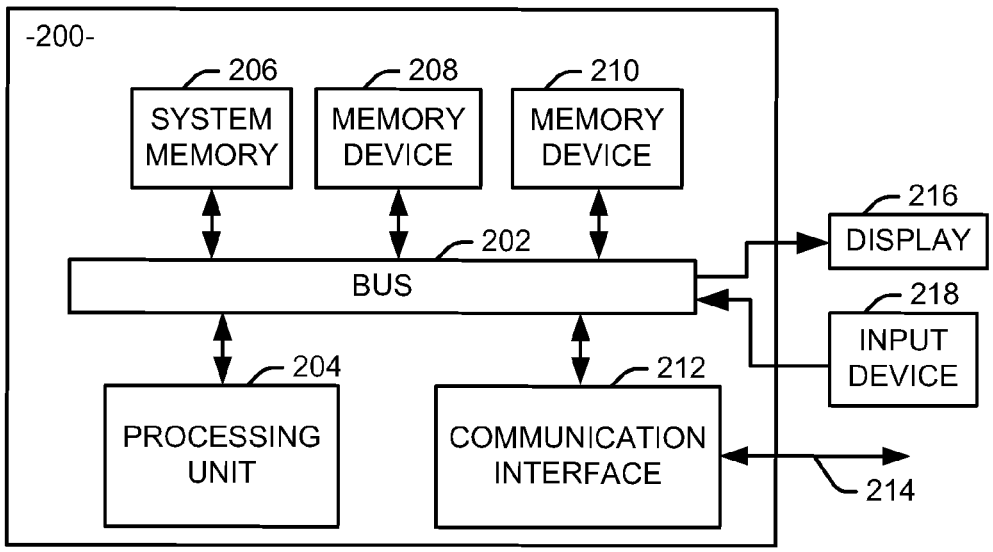
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 200 of hardware components capable of implementing examples of the systems and methods disclosed in FIGS. 1-4, such as the imager interface 14, the system control 16, and the color selection component 18 of FIG. 1. The system 200 can include various systems and subsystems. The system 200 can be a personal computer, a laptop computer, a workstation, a computer system, an appliance, a "smart" phone, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand-alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a foreign object detection system. Computer executable logic for implementing the system control 126 resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can include either a single medium or multiple non-transitory media operatively connected to the processing unit 204.

The invention has been disclosed illustratively. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed.

Having described the invention, we claim:

1. A method for detecting foreign objects in or on a subject of interest, the method comprising:
    capturing a first set of images of a sample subject known to be free of foreign objects;
    classifying a plurality of colors from a defined color palette according to a color content of the first set of images into at least first and second classes;
    capturing a second set of images of the subject of interest; and
    determining if a foreign object is present in or on the subject of interest if a color from the first class is present in the second set of images.

2. The method of claim 1, wherein classifying a plurality of colors from a defined color palette according to a color content of the first set of images comprises classifying the plurality of colors via a naïve Bayesian classification.

3. The method of claim 1, wherein classifying a plurality of colors from a defined color palette according to a color content of the first set of images comprises assigning all colors of the plurality of colors appearing in the first set of images to the second class and all other colors of the plurality of colors to the first class.

4. The method of claim 1, further comprising indicating a location of a foreign object to a user if the foreign object is determined to be present.

5. The method of claim 4, further comprising:
    receiving feedback from the user that the foreign object determined to be present is not a foreign object;
    determining a set of colors associated with the foreign object; and
    transferring the determined set of colors from the first class to the second class.

6. The method of claim 4, wherein indicating a location of a foreign object to a user comprises displaying a given image of the second set of images to the user with the location of the foreign object displayed in color and a remainder of the image displayed in grayscale.

7. The method of claim 4, wherein indicating a location of a foreign object to a user comprises displaying a given image of the second set of images to the user with the location of the foreign object highlighted in a preselected color.

8. The method of claim 4, wherein indicating a location of a foreign object to a user comprises displaying a text message to a user.

9. A method for detecting foreign objects in or on a subject of interest, the method comprising:
    capturing a plurality of intensity values for each pixel of a first set of images of a sample subject known to be free of foreign objects, each of the plurality of intensity values being associated with a specific wavelength of visible, infrared, or ultraviolet light a first set of images;
    quantizing each of the plurality of intensity values to a desired resolution, such that a defined color palette according to the desired resolution and a number of intensity values in the plurality of intensity values for each pixel;
    classifying a plurality of colors from the defined color palette according to a color content of the first set of images into at least first and second classes;
    capturing a second set of images of the subject of interest; and
    determining if a foreign object is present in or on the subject of interest if a color from the first class is present in the second set of images.

10. The method of claim 1, wherein the subject of interest is the interior of an airplane, and the sample subject is a portion of the interior of the aircraft that has been previous inspected and found to be clear of foreign objects.

11. A system for detecting foreign objects in or on a subject of interest comprising:
    an imaging system;
    a system control configured to instruct the imaging system to capture a first set of images of a sample subject known to be free of foreign objects; and
    a color selection component configured to select a plurality of colors from a defined color palette according to a color content of the first set of images;
    wherein the system control is further configured to instruct the imaging system to capture a second set of images of the subject of interest and notify a user if a selected color is present in the second set of images.

12. The system of claim 11, wherein the imaging system, the system control, the color selection component, and the display are collectively implemented as a wearable computer with an optical head-mounted display.

13. The system of claim 11, wherein the color selection component is configured to select the plurality of colors from the defined color palette according to a color content of the first set of images by classifying the plurality of colors via a naïve Bayesian classification.

14. The system of claim 11, wherein the color selection component is configured to select all colors appearing the first set of images.

15. The system of claim 11, further comprising a user interface configured to receive one of a confirmation that the presence of the selected color represents a foreign object in or on the subject of interest and an indication that the presence of the selected color does not represent a foreign object.

16. The system of claim 15, wherein the selected color present in the second set of images is removed from the selected plurality of colors in response to the indication that the presence of the selected color does not represent a foreign object.

17. The system of claim 11, wherein a system control is configured to instruct the imaging system to capture a plurality of intensity values for each pixel of the first set of images, each of the plurality of intensity values being associated with a specific wavelength of visible, infrared, or ultraviolet light, and quantize each of the plurality of intensity values to a desired resolution, such that the defined color palette is defined according to the desired resolution and a number of intensity values in the plurality of intensity values for each pixel.

18. A non-transitory computer readable medium comprising:
    a system control configured to instruct an imaging system to capture a first set of images of a sample subject known to be free of foreign objects, the system control comprising an imager interface configured to receive the captured first set of images and a user interface configured to receive an input from a user; and a color selection component configured to classify a plurality of colors from a defined color palette according to a color content of the first set of images into at least first and second classes;

wherein the system control is further configured to instruct the imaging system to capture a second set of images of a subject of interest, notify a user when color from the first class is present in the second set of images, and receive an input from the user via the user interface indicating if the color represents a foreign object in the subject of interest.

19. The non-transitory computer readable medium of claim 18, wherein the color selection component is configured to assign all colors of the plurality of colors appearing in the first set of images to the second class and all other colors of the plurality of colors to the first class.

20. The non-transitory computer readable medium of claim 19, wherein, in response to an input for the user indicating that a color from the first class is not associated with a foreign object, the system control is configured to remove the color from the first class and add it to the second class.

* * * * *